United States Patent [19]

Romeo et al.

[11] Patent Number: 5,559,104
[45] Date of Patent: Sep. 24, 1996

[54] PROCEDURE FOR THE PURIFICATION OF HYALURONIC ACID AND FRACTION OF PURE HYALURONIC ACID FOR OPHTHALMIC USE

[75] Inventors: Aurelio Romeo, Rome; Silvana Lorenzi, Padua, both of Italy

[73] Assignee: Fidia S.p.A., Abano Terme, Italy

[21] Appl. No.: 439,437

[22] Filed: May 11, 1995

Related U.S. Application Data

[63] Continuation of Ser. No. 976,991, filed as PCT/EP92/00861, Apr. 16, 199 abandoned.

[30] Foreign Application Priority Data

Apr. 19, 1991 [IT] Italy ................... PD91A0077

[51] Int. Cl.$^6$ .................. A61K 31/725; C08B 37/08
[52] U.S. Cl. ................. 514/54; 514/62; 514/912; 536/53; 536/55; 536/55.1; 536/55.2; 536/55.3
[58] Field of Search ............... 536/53, 55, 55.1, 536/55.2, 55.3; 514/54, 62, 912

[56] References Cited

U.S. PATENT DOCUMENTS

| | | | |
|---|---|---|---|
| 4,141,973 | 2/1979 | Balazs | 514/54 |
| 4,920,104 | 4/1990 | DeVore et al. | 514/54 |

FOREIGN PATENT DOCUMENTS

| | | |
|---|---|---|
| 0138572 | 4/1985 | European Pat. Off. . |
| 0239335 | 9/1987 | European Pat. Off. . |
| 0265116 | 4/1988 | European Pat. Off. . |

OTHER PUBLICATIONS

T. C. Laurent, *Chem. and Mol. Biol. of Intracellular Matrix*, vol. 2, 1970, pp. 703–732.
Z. Ogawa et al. (Nippon Kayaku Co., Ltd.) JP 01 43,502 Chem. Abstr. 1989, vol. 111, No. 22, 201647a.
O. H. Lowry et al. The Journal of Biological Chemistry, vol. 193 (1951) pp. 265–275.
W. D. Comper et al. Physiological Reviews, vol. 58, No. 1 (1978) pp. 255–315.
K. Meyer Chemical Structure of Hyaluronic Acid, Fed. Proceed, vol. 17 (1958) pp. 1075–1077.
E. A. Balazs et al. Mod. Probl. Ophthal. vol. 10 (1972) pp. 3–21.
U. B. G. Laurent Arch Ophtalmol., vol. 101 (1983) pp. 129–130.
D. Miller et al. Ophtalmic Surgery, vol. 8, No. 6 (1977) pp. 58–61.
D. Miller et al. Ophtalmic Surgery, vol. 11, No. 1 (1980) pp. 19–21.
E. L. Graue et al. Exp. Eye Res, vol. 31 (1980) pp. 119–127.
L. Ozaki et al. Folia Ophthalmological Japonica, vol. 32 (1981) pp. 1301–1305.
M. S. Norn Acta Ophthalmologica, vol. 59 (1981) pp. 587–594.
F. M. Polack et al. Ophthalmology, vol. 88, No. 5, (1981) pp. 425–431.
C. D. Binkhorst Am. Intra–Ocular Implant. Soc. J., vol. 6. No. 4 (1980) pp. 340–341.
L. G. Pape Am. Intra–Ocular Implant. Soc. J., vol. 6, No. 4 (1980) pp. 342–343.
M. S. Passo et al. ARVO Abstracts, 10, 10:45 (1981).
P. Percival Trans. Ophthal. Soc. UK, vol. 102, No. 2 (1982) pp. 294–297.
S. M. McRae et al. American Journal of Ophthalmology, vol. 95 (1983) pp. 332–341.
F. G. Berson et al. American Journal of Ophthalmology, vol. 95 (1983) pp. 668–672.
CA 111:201647a Z. Ogawa et al. –JP 01 43,502 (Nippon Kayaku Co., Ltd).
CA 104:24071r M. Ishioroshi (Q.P. Corp.) JP 60,149,601.
CA 112:79852s R. Numazawa et al. (Mitsubishi Rayon Co., Ltd.) JP01,210,401.
CA 102:84389u Ichimaru Farukosu K.K.–JP 59,166,504.

*Primary Examiner*—Gary L. Kunz
*Assistant Examiner*—Kathleen Kahler Fonda
*Attorney, Agent, or Firm*—Birch, Stewart, Kolasch & Birch, LLP

[57] ABSTRACT

A highly pure fraction of hyaluronic acid is disclosed which is non-inflammatory and avoids post-operative complications in ocular surgery. Also disclosed is a process for the preparation of hyaluronic acid characterized by converting hyaluronic acid into a corresponding quaternary ammonium salt and, following purification procedures, reconverting the quaternary ammonium salt into a sodium salt of hyaluronic acid.

25 Claims, No Drawings

PROCEDURE FOR THE PURIFICATION OF HYALURONIC ACID AND FRACTION OF PURE HYALURONIC ACID FOR OPHTHALMIC USE

This application is a continuation, of patent application Ser. No. 07/976,991 filed on as PCT/EP92/00861 on Apr. 16, 1992, now abandoned.

BACKGROUND AND FIELD OF THE INVENTION

The present invention relates to a new procedure for the preparation of highly pure fractions of hyaluronic acid and its salts. Moreover, the invention encompasses a specific fraction of hyaluronic acid and its salts, in particular its sodium salt, obtainable by said procedure and having an average molecular weight within a specified range.

Hyaluronic acid (HA) is a typical and important representative of a class of biological macromolecules known as glycosaminoglycans (mucopolysaccharides). HA is a biological polymer which is present, with identical molecular structure, in all connective tissues of vertebrate organisms, where it plays a structural and biological role, in the sense that its local levels are strictly correlated with the tonus, trophism and tissue repair in case of injury. A review on the physiological role of these biological substances was given in Phys. Rev. (Comper W. D., Laurent T. C.: Physiological function of connective tissue polysaccharides. Phys. Rev., 58, (1), 255–315, 1978). The chemical-physical nature of HA is that of a saccharide biopolymer (D-glucuronic acid and N-acetylglycosamine), polymerized in alternation, forming long, unbranched molecular chains varying in molecular weight to a maximum of 8,000,000 Daltons (Meyer K.; Chemical Structure of Hyaluronic Acid. Fed. Proceed. 17, 1075, 1958; Laurent T. C.; Chemistry and Molecular Biology of Intracellular Matrix, 703–732, Academic Press N.Y., 1970). The behavior of this biopolymer in aqueous solution guarantees a particular viscosity, called visco-elasticity, which is typical of some biological fluids, such as synovial fluid and vitreous fluid, where HA is present at a concentration of 0.12–0.24% (Balazs E. A. et al.: Hyaluronic acid and replacement of vitreous and aqueous humor. Mod. Probl. Ophthal., 10, 3–21, 1972). Also aqueous humor, of human origin, was found to contain HA in an average concentration of 1.14 mcg/g (Laurent U. B. G.: Hyaluronate in human aqueous humor. Arch. Ophthalmol., 101, 129–130, 1983).

A body of published evidence has accumulated showing that the local supply of exogenous HA has distinct therapeutic and protective benefits in a great variety of pathological conditions of connective and epithelial tissues, such as:

impaired tissue regeneration in non-healing skin ulcers;
arthrosic degeneration of articular connective tissue;
ocular surgery.

Particularly appreciated is the possibility, provided by the visco-elastic nature of HA, to coat the tissues exposed to risk of damage during surgical manipulation. According to surgeons who have used HA, the presence of a viscous layer of exogenous HA on the tissues which are most exposed to traumatizing accidental contacts, such as the cornea, exerts an efficient protective influence, which is reflected to a very positive degree in the successful outcome of the operation.

The protective effect and the facilitatory influence on tissue repair exerted by exogenous HA on the cornea has been shown both in experimental animals (Miller D. et al.: Use of Na-hyaluronate during intraocular lens implantation in rabbits. Ophthalmic Surgery, 8, (6), 58–61, 1977; Miller D. et al.: Use of Na-hyaluronate in autocorneal transplantation in rabbits. Ophthalmic Surgery, 11, (1), 19–21, 1980; Graue E. L. et al.: The protective effect of Na-hyaluronate to corneal endothelium. Exp. Eye Res., 31, 119–127, 1980; Ozaki L. et al.: Protective effect of Healon-coated intraocular lens on the corneal endothelium. Folia Ophthalmologica Japonica, 32, 1301–1305, 1981) and in man (Norm M.: Preoperative protection of cornea and conjunctiva. Acta Ophthalmologica, 59, 587–594, 1981; Polack F. M. et al.: Sodium hyaluronate (Healon) in keratoplasty and IOL implantation. Ophthalmology, 88, 425–431, 1981).

Several procedures are known for the preparation of purified hyaluronic acid and of particular fractions with a high degree of purity to be used in therapy, for example in the aforesaid indications.

The molecular fractions of integral hyaluronic acids obtained directly by extraction of organic materials, for example from hens' crests, have molecular weights which can vary within wide limits, for example from about 90% –80% to 0.2% of the molecular weight of the integral acid, preferably between 5% and 0.2%. The fractions can be obtained from the integral acids with hydrolyzing or oxidizing or enzymatic chemical agents or physical procedures, for example mechanical or by irradiation, and often, therefore, primordial extracts are formed in these same purification procedures (see for example the article by Balazs et al. in "Cosmetics & Toiletries". Italian edition No. 5/84, pp 8–17). The separation and purification of the molecular fractions obtained is effected by the known techniques.

For example, in U.S. Pat. No. 4,141,973, a procedure is described for the preparation of hyaluronic acids with a molecular weight of at least 750,000 Daltons which can be used, in view of their particular and high degree of purity and for the absence of inflammatory effects, in operations on the eye. The procedure consists of extracting the PEA sodium salt from the starting material, eliminating blood residues from the animal organs used, deproteinizing the extract thus obtained, eliminating inflammatory impurities, treating the product in aqueous solution with a sterilizing agent and in precipitating the hyaluronic acid salt from the aqueous solution with an organic solvent. The blood residues are eliminated with ethanol, HA in the form of its sodium salt (which is the form in which it is found in the starting materials) is extracted with water, deproteinization is effected by treatment with diluted acids and simultaneous extraction of the hydrolyzed parts with chloroform, or by means of proteolytic enzymes, harmful inflammatory substances are eliminated by extraction with chloroform at pH 6–7 and sterilization is effected by treatment with cetylpyridinium chloride. By this procedure, the only hyaluronic acid fraction obtained is that specifically described in the patent as having a molecular weight of 1,586,000 Daltons. On the basis of its chemical, physical and biological properties, this molecular fraction of hyaluronic acid seems to correspond to the commercial product known by the trademark HEALON®.

New techniques have been developed, such as molecular ultrafiltration. By this means of purification it is possible to discard those HA fractions with a molecular weight coming within the higher or lower margins of the range of molecular sizes. For example, in the EPO patent No. 01238572, granted on 25.7.1990, a procedure is described to obtain fractions of sodium hyaluronate with mean molecular weights of between 250,000 and 350,000 Daltons, by exposing the product directly obtained by extraction of organic material and subsequent enzymatic deproteinization with papain, to two molecular ultrafiltrations through membranes with a molecular cutoff of 30,000, that is, with membranes which trap only those fractions with molecular weights of over 30,000. This fractioning appears to be important to the obtainment of a product free from secondary actions of an inflammatory nature, since the fractions responsible for such effects are those with low molecular weights, for example about 30,000 Daltons. After further molecular filtration, using membranes with an exclusion limit of 200,000 (that is, membranes which trap those fractions with molecular weights of over 200,000 Daltons) the obtained filtered product is a fraction (called in the patent HYALASTINE) with a mean molecular weight between 50,000 and 100,000 Daltons, while the portion left on the membrane is a sodium hyaluronate fraction which has a mean molecular weight between 500,000 and 730,000 (the fraction called HYAL-RCTIN).

SUMMARY OF THE INVENTION

The present invention provides another method for the preparation of a fraction of hyaluronic acid which is highly pure and has a specified molecular weight range. This fraction has an interesting application in ophthalmic surgery: this solution is extremely well tolerated, it is not inflammatory and it does not cause post-operative complications. Furthermore, the product offers the considerable advantage of being able to be left in situ after surgery without causing post-operative complications such as especially too-high ocular tension, thus reducing the risks involved by handling during its removal, as has been the practice till now. This new fraction of pure hyaluronic acid, in the form of its sodium salt, will be called by the name of "HA-1" in the following description.

DETAILED DESCRIPTION OF THE INVENTION

According to the discovery of the present invention it is possible to intervene to advantage in the procedures of purification of integral hyaluronic acids or their salts, especially alkaline salts, such as firstly sodium salt, with conversion of such acids or salts into quaternary ammonium salts of a given type. Such salification can be effected at any one stage of the purification procedure. Since these quaternary ammonium salts are easily soluble in certain organic solvents, such as aprotic solvents, such as especially N-methylpyrrolidone, they can be extracted with such solvents from the aqueous phase, thus effecting a special and additional purification with regard to the techniques described in the prior art, an operation which is apparently responsible for the degree of purity of the products obtained at the end of the procedure. The conversion of the hyaluronic component into quaternary ammonium salts can be done for example by treating the aqueous solution of the sodium salt, containing other salts, such as especially NaCl, using a reactor or a column containing a macromolecular, sulfonic ion exchanger in salified form with quaternary ammonium bases, for example a DOWEX® M-15 resin, prepared in the form of tetrabutylammonium salt, obtainable by treatment of the sulfonic resin with quaternary ammonium hydroxides, for example tetrabutylammonium hydroxide. The ammonium salt passes into the eluate and is eluted completely by the ion exchanger with water. This aqueous extract is evaporated to dryness and the residue constituted by the ammonium salt of the polysaccharide is dissolved in one of the aforesaid solvents, then the insoluble solid parts are filtered.

The procedure of the present invention is therefore characterised, in its more general aspect, by purifying a hyaluronic acid or one of its molecular fractions or one of their salts by their conversion into a corresponding quaternary ammonium salt with lower ($C_{1-6}$) aliphatic hydrocarbyl substitutes.

Secondly, the procedure is characterized by the gathering of the quaternary ammonium salt of hyaluronic acid or one of its molecular fractions in an organic solvent which is able to dissolve such salts and by recovering from the filtered solution the hyaluronic acid or its molecular fraction in the form of a metal salt, and, if desired, by submitting the salts thus obtained to further purification for example in a way which is per se already known.

The invention therefore concerns the use of the quaternary ammonium salts of hyaluronic acids both in the procedures of extraction of the polysaccharide from the animal organs and from the total extracts, where the purification according to the invention can be done at any suitable stage of the procedure, including the operations in which fragmentation and separation of molecular fractions are effected, and in any further processing of such fractions, and in the further purification of already isolated fractions, pure or not pure, new or known.

As previously said, conversion of the hyaluronic polysaccharide can be effected at any suitable stage of the purification procedure, and one skilled in the art will be able to choose when this should be in each particular case, according to the criteria dictated by the particular combination of the various known steps which have been chosen. These conventional and known steps include, essentially and in general:

1) Extraction of the polysaccharide (generally and prevalently in its sodium salt state) from the animal organs, previously minced and homogenized. This is usually done by means of an organic solvent which can be mixed with water, such as an aliphatic alcohol or a lower ($C_{3-6}$) aliphatic ketone, such as ethanol or acetone.
2) Elimination of protein substances by extraction with suitable solvents or by digestion of an aqueous solution of the extract obtained in 1) with a proteolytic enzyme, such as papain, pepsin, trypsin or pronase, in the presence of a buffer, for example cysteine hydrochloride-phosphate,
3) Dialysis of an extract obtained according to 1) or 2).
4) Sterilization of a solution obtained at any one of the previous stages with a known bactericide, for example cetylpyridinium chloride in sodium chloride solution. This operation is usually repeated several times.
5) Separation of hyaluronic polysaccharide fractions or their respective salts with different molecular weights or, respectively, elimination of undesired fractions, for example with marginal molecular weights, that is, too far removed from the declared molecular size range. This operation is carried out preferably by molecular ultrafiltration, for example in the known way.
6) Isolation of the purified fraction or of the respective salt (for example sodium salt) from the aqueous solution by precipitation with a suitable organic solvent, for example with an alcohol.

The sequence of these steps, and possibly also of others already used in the prior art or elaborated by experts in the field, can be largely varied. The specific step of the present invention, that is, the salification of quaternary ammonium ions, can be inserted at will and advantageously wherever one would expect the greatest technical effect.

The ammonium salt of the polysaccharide component can be directly removed from the resin of the ion exchanger with the aforesaid solvents which are capable of dissolving such salts, such as those specified hereafter, but preferably the ammonium salt is extracted first with water, then the obtained solution is evaporated to dryness. The ammonium salt thus isolated is gathered in the aforesaid solvents and the solution is then filtered.

One particular way of effecting the procedure of the present invention derives from the insertion of the salification with quaternary ammonium ions in the combination of the aforesaid operation, in the aforesaid order, between steps 2) and 3). Apart from the known purification techniques and the specific step of the present invention, that is, conversion of the metal salts of hyaluronic acid into quaternary ammonium salts, it is possible, according to another particular aspect of the present invention, to make use of chelating agents for iron ions, preferably in the aforesaid extraction step 1). In fact it is known that iron ions, always present in original hyaluronic acid extracts, deriving from blood residues from the animal organs used, are responsible for depolymerization processes of the polysaccharide chain. The elimination of metal ions has proved very useful in the obtainment of hyaluronic fractions with relatively high molecular weights, and this can be achieved by chelation. By taking this measure it is possible not only to obtain hyaluronic acids or their salts with possibly high molecular weights, but also particularly pure products which are stable in aqueous solutions thanks to the total absence of the aforesaid iron ions.

A preferential object of the invention therefore is constituted by a procedure characterised by extracting animal organs containing hyaluronic acid and/or one of its salts with an organic solvent which can be mixed with water in the presence of chelating agents for iron ions, repeating the operation until there are no more iron ions, by gathering the previously dried residue of these washings in an aqueous solvent in the presence of a proteolytic agent and a suitable buffer, and passing the solution, previously freed from any solid residues, on an ion exchanger constituted by a macromolecular sulfonic resin in the form of one of its quaternary ammonium salts with lower ($C_{1-6}$) aliphatic groups. The eluate extracted from the ion exchanger is then dried and dissolved in an organic solvent able to dissolve the quaternary ammonium salts of hyaluronic acids and fractions thereof. Ammonium salt is then transformed into a sodium salt by addition of an aqueous solution of a sodium halogenide, such as sodium chloride or sodium bromide, to the organic solution. The thus obtained aqueous solution of the sodium salt is then extracted with organic solvents which cannot be mixed with water, and optionally subjected to repeated dialysis. The obtained solution is then treated with a sterilizing agent, and, if desired, the solution obtained after sterilization can be submitted to ultramolecular filtration. Any undesired hyaluronic polysaccharide fractions are then discarded and the desired fractions of the sodium hyaluronate are isolated in a per se known way.

The solvents to use according to the present invention to dissolve the quaternary ammonium salts are aprotic solvents, such as N-alkylpyrrolidones, in particular N-methylpyrrolidone, dialkylsulfoxides, dialkylcarboxylamides, such as in particular lower ($C_{2-6}$) dialkylsulfoxides, especially dimethylsulfoxide, and lower ($C_{2-6}$) dialkylamides of lower ($C_{1-6}$) aliphatic acids, such as dimethyl- or diethylformamide- or dimethyl- or diacetylacetamide.

The tetraalkylammonium bases used to prepare the ion exchanger resin and therefore characteristic hyaluronic ammonium salts of the invention are bases with lower aliphatic groups, preferably alkyls with between 1 and 6 carbon atoms. Most preferably, the salified resin with the tetrabutylammonium ion is used.

In the aforesaid combinations used for the procedures of extraction, purification and isolation of the hyaluronic acids, of their molecular fractions and their salts, and in particular in the aforesaid combination, which forms a preferential procedure according to the invention, it is preferable to use the following agents.

(a) for extraction of the starting material constituted by animal organs: ethanol or acetone.

(b) as chelating agent for iron ions: 1,10-phenanthroline or dimethyl derivative.

(c) as proteolytic agents: those already mentioned.

(d) as solvents for the quaternary ammonium salts: N-methylpyrrolidone or dimethylsulfoxide.

(e) as solvent for the purification of the aqueous extract of sodium salt obtained from the organic solution of the ammonium salts: methylene chloride, ethyl acetate.

(f) as sterilizing agent: cetylpyridinium chloride in the presence of phosphate buffer.

(g) as organic solvent to precipitate the sodium salt from the purified aqueous solution, possibly after ultrafiltration: ethanol.

In the aforesaid procedures it is possible to introduce also variations which can be of further use in the successful obtainment of even purer final products. For example, the use of sterilizing agents of the aforesaid type, that is, quaternary ammonium salts with heterocyclic nuclei and containing long-chained alkyls (for example cetyl), such as the cited cetylpyridinium chloride, can at the same time serve as a purification step, since the addition of these to a solution of sodium hyaluronate produces the corresponding ammonium salt with the ion of hyaluronic acid. These salts precipitate in aqueous solution and this treatment therefore makes it possible to obtain, by subsequent repeated reprecipitations and washings of the precipitates, and then by dissolving in NaCl solution, a solution of sodium hyaluronate from which to isolate ultrapurified products. These products are especially suitable for use in ophthalmic surgery.

The molecular ultrafiltration is carried out in a per se known way. That is, membranes are used which trap, for example, those fractions with higher molecular weights, for example over 200,000 and, if desired, the separated fractions can be recovered both from the filtered product and from the membrane. A particularly interesting way of effecting the procedure of the present invention is to combine the aforesaid chemical operations of purification with a molecular ultrafiltration which eliminates hyaluronic fractions with low molecular weights. Such fractions are recognized as being responsible for the onset of inflammatory effects in products for thereapeutic purposes, as reported in the case of the fractions described in the aforesaid EPO Patent No. 0138572, granted on 25.7.1990.

Another preferred object of the present invention is, therefore, the aforesaid procedure regarding a detailed combination of the purification operations in which, in the optional part, molecular ultrafiltration is effected to eliminate low-molecular-weight molecular fractions, especially fractions with molecular weights of less than 30,000. By this procedure, or more precisely, by following the details described in illustrative Examples 1 and 2, a fraction of sodium hyaluronate is obtained which is very valuable from a therapeutic point of view and which, as was said initially, bears the name HA-1. It is particularly interesting for its use in ocular surgery.

Use of the Product in Ocular Surgery

The hyaluronic acids described in the literature and recommended for use in operations to the eye do not satisfy criteria of absolute perfection, especially since they cannot be left in place after surgery, for example after cataract surgery, because of the presence of both residues or traces of inflammatory substances and components with molecular weights that are too high and therefore have a limiting viscosity number of more than 21 dl/g. Moreover they can cause, as said before, an undesired and dangerous increase in ocular pressure.

The exogenous HA introduced in the anterior chamber during surgery should not exert negative effects on post-surgery intraocular pressure, nor trigger inflammatory sequences in the intra-ocular environment. The former adverse effect has repeatedly been described in the literature after use of very high molecular weight HA having an extremely elevated degree of viscosity (Binkhorst C. D.: Inflammation and intraocular pressure after the use of HEALON® in intraocular lens surgery. Am. Intra-Ocular Implant. Soc., J., 6, (4), 340–341, 1980; Pape L. G.: Intracapsular and extracapsular technique of lens implantation with HEALON® Am. Intra-Ocular Implant. Soc. J., 6, (4), 342–343, 1980; Passo M. S. et al.: Intraocular pressure following cataract surgery using HEALON®. ARVO abstracts, 10, 10:45, 1981; Percival P.: Experiences with the Boberg Aris lens and sodium hyaluronate (Healonid). Trans. Ophthal. Soc. UK, 102, (2), 294–297, 1982; McRae S. M. et al.: The effects of sodium hyaluronate, chondroitin sulphate, and methylcellulose on the corneal endothelium and intraocular pressure. Ann. J. Ophthalmol., 95, 332–341, 1983).

This experience led to the recommendation to remove the substance by rinsing with physiological saline after the operation. Berson et al (Berson F. G. et al.: Obstruction of aqueous outflow by sodium hyaluronate in enucleate human eyes. Am. J. Ophthalmol., 95, 668–672, 1983) studied the mechanism of this adverse event in post-mortem enucleated human eye and suggested that the underlying cause was mechanical obstruction of physiological drainage facilities in the anterior chamber, due to the extreme viscosity of the substance introduced.

The sodium hyaluronate fraction described in U.S. patent by Balazs, U.S. Pat. No. 4,141,973, and having a molecular weight of 1,586,000 (see column 13 of the same patent) is a product which seems, in view of its indicated physical-chemical and biological properties, to be the best ocular product on the market. It is known by the name of HEALON® and is not immune from the aforesaid disadvantage. That is, its molecular weight is essentially too high and it therefore has inadequate viscosity for certain operations to the eye.

Indeed, although the test used in that patent (to measure the antiphlogistic effect) gave good data, HEALON® cannot be left in situ after surgery, for example after operations for cataract, since it would cause post-operative complications, such as a rise in ocular pressure.

In U.S. Pat. No. 4,920,104 by Dale P. De Vote (assigned to Med Chem Products, Inc. Acton, Mass.) a viscoelastic solution of sodium hyaluronate in physiological saline solution is described and claimed which has a kinematic viscosity of between 45,000 and 64,000 centistokes and contains a sodium hyaluronate with a mean molecular weight in the range of 1,000,000 to 2,000,000 Daltons. This product too is declared for use in surgical operations to the eye, where it can be used more advantageously than other preparations, due to its minor post-operative side effects, especially as the rise in post-operative ocular pressure is contained.

However, this product too must be eliminated after surgery, as can be seen from Tables 2 and 3 in column 4 of the patent, while Table 1 shows that there is a rise in ocular pressure after surgery if the product is left in situ.

Another fraction of sodium hyaluronate for use in ophthalmology is described in European patent No. 0138572 and has a mean molecular weight which varies between 500,000 and 730,000 Daltons (HYALECTIN). It can be used conveniently to substitute for the endobulbar fluids, and is also used in operations to the eye, such as for cataract and ocular implants. There was however a need for products with greater visco-elasticity which were able to maintain the correct spaces within the anterior chamber during surgery, to counterbalance the vitreous response, to have an efficacious protective effect on the endo-ocular structure without having to be removed after surgery. As we have seen, the products with high molecular weights described in the literature and used in the aforesaid operations on the eye always had to be removed after surgery. The merit of the present invention lies in the fact that an original procedure has been elaborated for the obtainment of fractions of sodium hyaluronate with a relatively high molecular weight, obtained by adding chelating agents for iron ions to the extraction solution, thus preventing depolymerization to low-molecular-weight fractions, free from those impurities or fractions which made it impossible to leave the product in the organism. The new fraction HA-1 of the present invention therefore represents an interesting novelty and great step forward in the art.

The fraction "HA-1" of the present invention, obtainable by the procedure described in Examples 1 and 2 has the following characteristics:

Viscosity: a limiting viscosity number ranging between 14.5 and 21 dl/g, when determined at 25° C. in 0.15M NaCl at pH 7.0 using an Ubbelhode suspended level viscosimeter. This corresponds to an average molecular weight ranging between 750,000 Daltons and 1,230,000 Daltons (preferably between 925,000 and 1,230,000 Daltons).

Protein content: a protein content not exceeding 0.2% expressed as albumin, when determined by the Lowry test (Lowry J. et al.; Protein Measurement with the folin phenol reagent. J. Biol., Chem. 193, 265–275, 1951).

U.V.: a U.V. absorbance at 257 nm (path length 1 cm) and at 280 nm not exceeding 1.0 A.U., when measured on a 1% w/V aqueous solution.

Dynamic viscosity: a dynamic viscosity of a 1% solution w/v in 0.15M NaCl at pH=7.0, not exceeding the following limits at the defined shear rates, using a rotational viscosimeter such as those described in the U.S. Pharmacopea XXII ed. (911) page 1619, at a temperature of 20° C.

| Shear rate | Dynamic viscosity (mPa · s at 20° C.) |
|---|---|
| $1\ s^{-1}$ | not more than 20000 mPa · s |
| $10\ s^{-1}$ | not more than 2000 mPa · s |
| $100\ s^{-1}$ | not more than 1000 mPa · s |
| $350\ s^{-1}$ | not more than 500 mPa · s |

Sulfated mucopolysaccharide: a content not exceeding 0.07% as sulfur, when determined on an inductively coupled plasma instrument (I.C.P.), using a suitable reference substance;

Iron: an iron content not exceeding 10 p.p.m., when determined by atomic absorption or I.C.P. technique.

Stability: a stability of buffered isotonic solutions with physiological pH of the fraction HA-1, naturally aged and heat-sterilized, determined by assessment of the limiting viscosity number and expressed with the corresponding decrease in mean molecular weight, not exceeding the following limits:

97% of the initial value (storage at 25° C. for 6 months)

75% of the initial value (sterilization at 118° C. for 32 min.)

80% of the initial value (sterilization at 121° C. for 16 min.)

90% of the initial value (sterilization at 124° C. for 8 min.)

The superior qualities of the hyaluronic fraction HA-1 of the present invention can be shown by the following experiments:

Intraocular Tolerability of heat sterilized solutions of HA-1 Fraction in Monkeys

OBJECTIVE

This test was carried out to evaluate ophthalmic tolerability in monkeys following the injection of HA-1 into the vitreous body of the eye.

MATERIALS AND METHODS

1. Test Species

Six young adult female cynomolgus (*Macaca fascicularis*) monkeys were used for this study. They were in good health and had no detectable eye lesions.

Primates were chosen for this study because they are considered to be the best species for studies on ophthalmic tolerability of viscoelastic products used for ophthalmic surgery.

The cynomolgus monkey was chosen because the Douroucoulis monkey, which was previously used for ophthalmic tolerability studies, is now an endangered species and comes under legal protection.

2. Experimental Groups and Relative Treatments
Group designation and dose levels The monkeys were treated once according to the following schedule:

| Animal Number | Dose level (ml) | Injection site right eye | Injection site left eye |
|---|---|---|---|
| 1 | 0.5 | saline | HA-1 |
| 2 | 0.5 | HA-1 | saline |
| 3 | 0.5 | saline | HA-1 |
| 4 | 0.5 | HA-1 | saline |
| 5 | 0.5 | saline | HA-1 |
| 6 | 0.5 | HA-1 | saline |

3. Compound Preparation and Administration

On the day of surgery the monkeys were anesthetized with ketamine hydrochloride supplemented with sodium pentobarbital. The pupils were then dilated with topical 1.0% tropicamide (Mydriacyl, Alcon Laboratories). The cornea, conjuctiva, adnexa and anterior segment were examined with the slit-lamp biomicroscope and the posterior segment with the indirect ophthalmoscope. The peripalpebral skin was prepared for surgery using two washes and flushes with 0.5% povidone iodine and sterile saline. A sterile drape and lid speculum were placed and the globe stabilized with a small tooth forceps. Sharp and blunt dissection was used to develop a limbal-based conjunctival flap, approximately 10 mm from and parallel to the superior limbus, approximately 10 to 15 mm in length. The dissection was carried through the conjunctiva and Tenoh's capsule to the episclera. The flap was prepared by dissecting anteriorly to the limbus exposing underlying sclera overlying the pars plana. Approximately 5–6 mm from the limbus, an intrascleral mattress suture of 7–0 Vicyrl (Ethicon) was placed, with the bites approximately 3 mm apart.

A 25-gauge needle was used to aspirate 0.5 ml of vitreous humor (in two animals it was possible to aspirate only 0.4 ml); the vitreous was replaced with an equal volume of HA-1 (12 mg/ml) in sterile saline of neutral pH or sterile saline. The mattress suture was secured to prevent leakage and the conjunctival flap was replaced. Antibiotic ointment was applied topically. Vitreous cell counts were performed on aspirated vitreous using a hemacytometer prior to administration and at approximately 48 hours post-administration.

4. Observations and Records

Approximately 48 hours after surgery, the animals were anesthetized and an ophthalmoscopic examination performed. Anesthesia, dilation and examination were performed as previously described. The examination was conducted in a blind fashion with regard to whether the eye in question was injected with HA-1 or control material. Ocular parameters were graded as shown in the standard key to ocular scoring scales shown below.

Conjunctival edema, injection and discharge; corneal edema, heme, cells, and flare:

0=normal

+1=mild

+2=moderate

+3=severe or extensive

Vitreous clarity:

0=clear

1=slight haze—fundus visible

2=moderate haze—fundus barely visible

3=haze—red fundus reflex

4=haze—gray fundus reflex

5=fundus not visible

The eyes were prepared for aspiration using a povidone iodine solution as previously described. A lid speculum was placed and the globe stabilized with a small tooth needle holder. Vitreous (0.1 to 0.2 ml) was aspirated directly through the conjunctiva and sclera, 6 mm from the limbus in the superior temporal quadrant. Care was taken to avoid the original surgical site. Inflammatory cells were counted using the hemacytometer. Topical antibiotic ointment was again applied.

RESULTS

The data (Table 1) demonstrate that HA-1 was very well tolerated and produced no significant ocular irritation when compared to the control article (saline).

Two animals in the saline group demonstrated mild aqueous cell infiltration and flare. Control vitreous white cell counts ranged from 10 to 60 cells per $mm^3$. One HA-1-injected eye showed mild aqueous cell infiltration and flare. Vitreous white cell counts ranged from 0 to 30 cells per $mm^3$ in test eyes.

TABLE 1

| Time | Conjuctiva | | | Cornea | Anterior chamber | | | Lens | Vitreous | |
|------|------|------|------|------|------|------|------|------|------|------|
| (hr) | Edema | Injection | Discharge | Edema | Heme | Flare | Cell | Cataract | Clarity | Cell count |
| RE | | | | | | | | | | |
| 0 | 0/6 | 0/6 | 0/6 | 0/6 | 0/6 | 0/6 | 0/6 | 0/6 | 0/6 | 0(1/6); 10 WBC - few RBC (1/6); 10 WBC - many RBC (1/6); 0 WBC - few RBC (3/6) |
| 48 | 0/6 | 0/6 | 0/6 | 0/6 | 0/6 | +1/6 | +1/6 | 0/6 | 0/6 | 0(2/6); 20 WBC (2/6); 10 WBC (1/6); 10 WBC - few RBC (1/6) |
| LE | | | | | | | | | | |
| 0 | 0/6 | 0/6 | 0/6 | 0/6 | 0/6 | 0/6 | 0/6 | 0/6 | 0/6 | 0(2/6; 0 WBC - few RBC (2/6); 10 WBC - many RBC (2/6) |
| 48 | 0/6 | 0/6 | 0/6 | 0/6 | 0/6 | +2/6 | +2/6 | 0/6 | 0/6 | 0-5-10-15-30-60 WBC* |

RE = Right eye (injected with 0.5 ml saline)
LE = Left eye (injected with 0.5 ml HA-1
WBC = White blood cell
RBC = Red blood cells
*single values for each monkey Therefore, compared to the saline controls, it can be concluded that HA-1 is extremely well tolerated by the ocular tissues following intravitreal replacement.

Efficacy of HA-1 vs HEALON® in surgery for extracapsular cataract extraction with posterior chamber intraocular lens implantation clinical study.

OBJECTIVE

The experiments described hereafter evaluated the efficacy and safety of HA-1 compared to the leading marketed viscoelastic material (HEALON®) in cataract extraction and intraocular lens implantation in two clinical studies. In the first clinical study, HA-1 and HEALON® were tested in the same experimental conditions (both aspirated after surgery). The second study focused in particular on the safety of HA-1 in regard to the rise in postoperative intraocular pressure and endothelial cell counts: in this second study (in which, unlike the first, where both the viscoelastic materials were aspirated after surgery) HA-1 was not removed at the conclusion of surgery, unlike HEALON®, which was aspirated from the eye.

MATERIALS AND METHODS

1. Study Designs

The design for both studies was randomized, parallel group, masked-observer (separate investigators did the follow-ups), evaluation of HA-1 vs HEALON® in extracapsular cataract extraction with posterior chamber intraocular lens implantation. In each study, patients with a primary diagnosis of senile cataracts and over 18 years of age were eligible.

In particular:

In the first study, 217 patients were recruited and randomization was done according to a ratio of about 3:1 (HA-1 161 patients, HEALON® 56 patients). Both viscoelastic materials were aspirated following surgery. The study period encompassed presurgery evaluation, the operative procedure and the immediate post-surgical follow-up period. In this study intraocular pressure was measured at 3 hours post-operatively and follow-up examinations at 1, 7 and 30 days post-operatively.

In the second clinical study 91 patients were recruited and randomized to HA-1(45) or HEALON® (46), according to a ratio of about 1:1. In this study HA-1 was not aspirated following surgery, unlike HEALON® which was aspirated as in the first study. The study period (and the relative study material for HA-1) were as previously described for the first study. In this study, post-operative intra-ocular pressure was measured at 1, 3, 6 and 9 hours post-operatively (more frequently than in the first study) and follow-up examinations at 1, 7, 30 and also 90 days post-operatively. The study included too specular microscopy at baseline and 90 days post-operatively.

2. Data Analysis and Statistical Methods

Statistical analyses were performed to evaluate treatment group comparability (alpha=0.10) and safety and efficacy (alpha=0.05). Fisher's exact tests, t-tests, and descriptive statistics were employed to evaluate the data.

3. Study Population and Characteristics

A total of 301 patients were studied, of whom took part in the first study, and 87 took part in the second study.

| | 1st study | | | 2nd study | | |
|---|---|---|---|---|---|---|
| | HA-1 | HEALON® | Total | HA-1 | HEALON® | Total |
| Baseline | 158 | 56 | 214 | 41 | 46 | 87 |
| Day 1 | 158 | 56 | 214 | 41 | 46 | 87 |
| Day 7 | 158 | 56 | 214 | 39 | 45 | 84 |
| Day 30 | 157 | 54 | 211 | 41 | 44 | 85 |

-continued

|  | 1st study | | | 2nd study | | |
| --- | --- | --- | --- | --- | --- | --- |
|  | HA-1 | HEALON ® | Total | HA-1 | HEALON ® | Total |
| Day 90 | — | — | — | 42 | 43 | 85 |

There were no substantial differences between the two treatment groups in either study, with regard to most demographic, medical or cataract characteristics.

4. Surgery

Preparation and methods: surgery was performed by the investigator's standard surgical technique for uncomplicated senile/adult extracapsular cataract extraction with posterior chamber intra-ocular lens transplantation. Pre-operative (prophylactic) medications, anaesthesia and other intra-operative medications were used according to the investigator's standard techniques but without the use of ocular antihypertensives. Pre-incision intra-ocular pressure was lowered as much as possible using a Honan intra-ocular pressure reducer, a "Super Pinky" or manual pressure. The viscoelastic substances (HA-1 and HEALON®) were used as described hereafter.

The products were removed after surgery, with the exception of HA-1 used in the second clinical trial which was left in place. Both HA-1 and HEALON® were inserted into the anterior chamber such as to facilitate surgical procedure and protect ocular tissues, in particular:
1st study:
the mean amount of HA-1 used (0.568 ml at a concentration of 12 mg/ml) was significantly greater than the amount of HEALON® used (0.439 ml at the concentration of 10 mg/ml), even though the difference was only of 0.129 ml.
2nd study:
there was no significant difference in the mean amount of viscoelastic used: in this case the mean amounts were 0.957 ml (HA-1) and 0,833 ml (HEALON®).

5. Assessments

The following tests were effected prior to, during and after surgery:
a) presurgical evaluation, for example to assess
   visual acuity (best manifest), tonometry, method of pachymetry (for corneal thickness) and slit lamp and ophthalmoscopic examination findings
   specular microscopy (2nd study only): endothelial cell counts were made using the specular microscope at 10 selected central corneal locations. Each count was adjusted by the appropriate factor to yield cell count per square millimeter and averaged to give a representative cell count per square millimeter.
b) Post-surgical evaluations, such as:
   intra-ocular pressure (by tonometry) was measured at:
   3 hrs post-operatively (1st study)
   1–3–6–9 hrs post-operatively (2nd study)
   ophthalmoscopic and slit lamp examinations, pachymetry, tonometry, specular microscopy (the last only for the 2nd study for endothelial cell counts) and visual acuity measurements (at follow-up examinations), were effected at:
   1–7–30 days in the first study
   1–7–30–90 days in the second study.

RESULTS

1. Operative Evaluation—Handling Characteristics of the Viscoelastic Materials Used The viscoelastics were rated as facilitating lens implantation in comparable proportions of each treatment group in both the clinical studies.

Post-operative Complications 2a) 1st clinical study
As can be seen from Table 2:
The highest percentage of complications (in 7.9% of all patients) occurred between surgery and day 1, while smaller percentages were reported at days 7 and 30.
At day 1 post-operatively the proportion of HEALON®-treated patients (14.3%) suffering complications was 2.5 times higher than for HA-1-treated patients (5.7%). This difference was statistically significant (p=0,079y by Fisher's two-tailed exact test). Differences on days 7 and 30 were not statistically significant (p>0.6 by Fisher's two-tailed exact test). Complications included intra-ocular pressure rises to 30 mmHg or more ($7/158$= 4.4% of HA-1-treated patients, $5/56$= 8.9% of HEALON®-treated patients) and corneal edema, iritis, conjunctivitis, hyphema, macular edema, wound leak, cyclitic membrane and subconjunctival hemorrhage.
As can be seen from Table 3, in which are reported tonometry data obtained presurgically and post-operatively (at 3 hrs and 1–7–30 days):
No significant differences in mean intra-ocular pressure occurred between treatment groups; however, HEALON®-treated patients had greater mean intra-ocular pressure rises at both 3 hrs and 1 day and had a significantly greater standard deviation of intraocular pressure than HA-1-treated patients at day 1.
The slit lamp, pachymetry (for corneal thickness) and ophthalmoscopic examinations revealed no differences between the two groups.
2b) 2nd clinical study
A slightly higher proportion of HEALON®-treated patients (37.0%) than HA-1-treated patients (28.6%) reported post-operative complications (Table 4). Complications included rises in intra-ocular pressure ($5/42$= 11.9% of HA-1-treated patients, $11/46$=23.9% of HEALON®-treated patients) and cases of hyphema, wound leak, vitreous hemorrhage, posterior capsule opacification, choroidal detachment, iris atrophy and macular edema.
The two treatment groups did not differ statistically with respect to either mean intra-ocular pressures or variability of the intra-ocular pressure at baseline or at any time from day 1 to day 90 (Table 5). During the first 9 hours after surgery, it appears that HEALON® (removed from the eye) and HA-1 (left in place) produced post-operative intra-ocular pressure distribution which differed primarily with respect to standard deviations. HEALON®-treated patients had greater standard deviations and a significantly higher mean value at 1 hour post-operatively and HA-1-treated patients had greater, but only marginally significant standard deviations, at 6 and 9 hours post-operatively. At 1 hr post-operatively, 22.7% of HEALON®-treated patients and 10% of HA-1-treated patients had intraocular pressures of 21 mmHg or more. At 6 hours and 9 hours post-operatively, comparable proportions of HA-1-treated (73.2% at 6 hours and 65.0% at 9 hours) and HEALON®-treated (68.2% at 6 hours and 71.4% at 9 hours) patients had pressure readings of 21 mmHg or greater.

No other difference was revealed between the two groups regarding the observations reported in the 1st study. Similarly, specular microscopy (endothelial cell count) revealed no significant differences (Tab. 6).

3. Quantitative Outcomes

The visual acuity assessments showed that efficacy of the two viscoelastic substances was comparable, in particular:
1st clinical study: There was no significant difference between the proportion of HEALON®-treated (77.8%) and HA-1-treated (84.7%) patients who achieved 20/40 visual acuity at day 30.
2nd clinical study: There was no significant difference between the proportion of HEALON®-treated (73.9%) and HA-1-treated (71.4%) patients who achieved 20/40 or better visual acuity at day 30. At day 90 the proportions were nearly identical.

TABLE 2

Post-operative complications: 1st clinical study

|  | HA-1 patients N = 158 N (%) | HEALON ® patients N = 56 N (%) | Total patients N = 214 N (%) |
|---|---|---|---|
| Day 1 |  |  |  |
| No | 149 (94.3) | 48 (85.7) | 197 (92.1) |
| Yes * | 9 (5.7) | 8 (14.3) | 17 (7.9) |
| Day 7 |  |  |  |
| No | 153 (98.1) | 55 (98.2) | 208 (98.1) |
| Yes | 3 (1.9) | 1 (1.8) | 4 (1.9) |
| Day 30 |  |  |  |
| No | 154 (98.1) | 52 (96.3) | 206 (97.6) |
| Yes | 3 (1.9) | 2 (3.7) | 5 (2.4) |

* The proportion of HEALON ®-treated patients with complications is significantly higher (p = 0.079 by Fisher's two-tailed exact test) than the proportion of HA-1-treated patients.

TABLE 3

Intra-ocular pressure assessment (tonometry in mmHg): 1st clinical study

| Treatment group | N | Mean | Standard deviation |
|---|---|---|---|
| Presurgery |  |  |  |
| Total | 213 | 16.671 | 3.598 |
| HA-1 | 157 | 16.682 | 3.747 |
| HEALON ® | 56 | 16.643 | 3.176 |
| 3-hour intraocular pressure |  |  |  |
| Total | 176 | 18.077 | 7.760 |

TABLE 3-continued

Intra-ocular pressure assessment (tonometry in mmHg): 1st clinical study

| Treatment group | N | Mean | Standard deviation |
|---|---|---|---|
| HA-1 | 129 | 18.027 | 7.417 |
| HEALON ® | 47 | 18.213 | 8.718 |
| Day 1 |  |  |  |
| Total | 212 | 19.146 | 7.497 |
| HA-1 | 157 | 18.580 | 6.865* |
| HEALON ® | 55 | 20.327 | 8.453 |
| Day 7 |  |  |  |
| Total | 200 | 14.431 | 3.979 |
| HA-1 | 148 | 14.468 | 4.147 |
| HEALON ® | 52 | 14.327 | 3.491 |
| Day 30 |  |  |  |
| Total | 207 | 15.002 | 3.730 |
| HA-1 | 154 | 14.932 | 3.744 |
| HEALON ® | 53 | 15.208 | 3.718 |

*Day 1 standard deviations of the two treatment groups are significantly different (p = 0.0508 by F-test).

TABLE 4

Postoperative complications: 2nd clinical study

|  | HA-1 patients N = 42 N (%) | HEALON ® patients N = 46 N (%) | Total patients N = 88 N (%) |
|---|---|---|---|
| Postoperative complications |  |  |  |
| No | 30 (71.4) | 29 (63.0) | 59 (67.0) |
| Yes | 12 (28.6) | 17 (37.0) | 29 (33.0) |

TABLE 5

Summary tonometry (mmHg) statistics by treatment group

| Treatment group | N | Mean | Standard deviation |
|---|---|---|---|
| Presurgery |  |  |  |
| Total | 86 | 15.256 | 3.365 |
| HA-1 | 40 | 15.575 | 3.296 |
| HEALON ® | 46 | 14.978 | 3.435 |
| 1-hour post-surgery |  |  |  |
| Total | 84 | 12.167 | 9.937 |
| HA-1 | 40 | 9.925* | 7.430** |
| HEALON ® | 44 | 14.206 | 11.473 |
| 3-hour post-surgery |  |  |  |
| Total | 84 | 23.012 | 14.244 |
| HA-1 | 41 | 22.805 | 15.481 |
| HEALON ® | 43 | 23.209 | 13.139 |
| 6-hour post-surgery |  |  |  |
| Total | 85 | 27.318 | 12.200 |
| HA-1 | 41 | 28.707 | 13.757*** |
| HEALON ® | 44 | 26.023 | 10.542 |
| 9-hour post-surgery |  |  |  |
| Total | 82 | 26.451 | 11.863 |
| HA-1 | 40 | 27.050 | 13.449**** |
| HEALON ® | 42 | 25.881 | 10.261 |

TABLE 5-continued

Summary tonometry (mmHg) statistics by treatment group

| Treatment group | N | Mean | Standard deviation |
|---|---|---|---|
| Day 1 | | | |
| Total | 87 | 20.839 | 8.868 |
| HA-1 | 41 | 21.805 | 9.474 |
| HEALON® | 46 | 19.978 | 8.301 |
| Day 7 | | | |
| Total | 84 | 14.381 | 5.411 |
| HA-1 | 39 | 15.051 | 5.973 |
| HEALON® | 45 | 13.800 | 4.865 |
| Day 30 | | | |
| Total | 83 | 14.313 | 3.732 |
| HA-1 | 40 | 14.825 | 3.761 |
| HEALON® | 43 | 13.837 | 3.683 |
| Day 90 | | | |
| Total | 80 | 13.138 | 3.252 |
| HA-1 | 39 | 13.128 | 3.357 |
| HEALON® | 41 | 13.146 | 3.190 |

*The two treatment groups differ significantly with respect to mean intraocular pressure (p = 0.0442 by t-test adjusted for unequal variances).
**The treatment groups' standard deviations are significantly different (p = 0.0070 by F-test).
***The treatment groups' standard deviations have a marginally significant difference (p = 0.0886 by F-test).
****The treatment groups' standard deviations have a marginally significant difference (p = 0.0898 by F-test).

TABLE 6

Summary of specular microscopy statistics by treatment group for endothelial cell count

| Treatment group | N | Mean | Stand. Dev. |
|---|---|---|---|
| Pre-surgery | | | |
| Total | 85 | 2283.1 | 451.24 |
| HA-1 | 40 | 2234.6 | 433.72 |
| HEALON® | 45 | 2326.1 | 466.86 |
| Day 90 | | | |
| Total | 80 | 2158.1 | 505.73 |
| HA-1 | 39 | 2068.2 | 585.52 |
| HEALON® | 41 | 2243.5 | 405.08 |

CONCLUSIONS

The results of the two clinical studies described herein show a valuable efficacy of the use of HA-1 in cataract extraction and intra-ocular lens implantation. In particular, it has been shown that HA-1 is well tolerated. In fact the product induces less post-operative complications (about 2.5 times less) than HEALON® tested in the same experimental conditions, that is, with removal of the substance after surgery (as described for the 1st clinical study). Among the post-operative complications, the increase in intra-ocular pressure should be considered particularly.

It should be noted that, in both studies, the post-operative course of patients treated with HA-1 and that of patients treated with HEALON® differed with regard to intra-ocular pressure. In the first study, in which both HA-1 and HEALON® were removed after surgery, a higher proportion of HEALON®-treated patients showed intra-ocular pressure increases of over 21 mmHg at day 1, compared to HA-1-treated patients. In the 2nd study, when HA-1 was not removed after surgery, unlike HEALON®, the post-operative intra-ocular pressure profiles of HA-1 were comparable.

It can therefore be concluded that some aspects of the two viscoelastic products are comparable, while they differ regarding post-operative complications: HEALON® removed from the eye seems to be linked with greater increases in intra-ocular pressure than HA-1 removed from the eye, and HA-1 left in place presents a post-operative intra-ocular profile comparable to that of HEALON® removed after surgery.

On the basis of these results, it is important to emphasize the possibility of leaving HA-1 in place without inducing post-surgical complications. This possibility offers the following valuable advantages:

1. It simplifies surgical procedure, since the step of extracting the product after surgery is omitted.
2. It lessens the risk of complications due to handling (that is, during aspiration). Examples of such risks are traumas due to surgical procedures and their relative consequences.

The present invention also concerns pharmaceuticl preparations containing, as the active ingredient, the new molecular fraction of hyaluronic acid in the form of its sodium salt, HA-1, especially in the form of saline solutions with neutral pH. The chosen concentration in HA-1 is such that the desired degree of viscosity is obtained, for example a viscosity of about 300 mPa $\times$s (at 350 s$^{-1}$) and about 10,000 mPa$\times$s (at 1 s$^{-1}$). All the solutions could be sterilized by heat.

The invention also concerns the use of the new sodium hyaluronate fraction HA-1 in eye surgery, especially in cataract operations or lens implants.

The following examples illustrate the invention:

Example 1—Procedure to Obtain HA-1 Fraction and its Relative Characterization Hen crests, either fresh or frozen (3000 g), are minced in a meat mincer and then carefully homogenized in a mechanical homogenizer. The resulting paste is placed in a glass container with 10 volumes of anhydrous acetone or ethanol containing 0.1% w/v of a specific iron chelating agent.

1,10-Phenanthroline (C.A.R.N. 66-71-7) or its dimethyl-derivatives are examples of useful chelating agents. Glass containers and specific ironchelating agents are used to avoid the depolymerization process of hyaluronic acid sodium salt, which could otherwise be caused by iron ions from steel containers or blood residues.

The hen crests are treated until complete extraction of the iron ions (Instrumental control: Absorbance of complex iron-chelating agent in acetone or ethanol phase in 1-cm cells at wavelength of maximum absorption (510 nm, in the case of 1,10-Phenanthroline, not more than 0.005 A.U.).

A further washing process is performed using the same volumes of anhydrous acetone (or ethanol) in order to remove any residue chelating agent. These treatments are carried out until the following test "A" results negative.

Test "A": 5 ml of acetone (or ethanol) phase are evaporated by means of moderate nitrogen flow. The residue is dissolved in 5 ml of water and the absorbance measured at wavelength of chelating agent maximum absorption.

The test is considered negative when absorbance is less than 0.1 A.U.

The final reaction product is stirred for 6 hours at a speed of 50 rpm and left to separate for 12 hours, after which the solvent is syphoned off and discarded.

This extraction process is repeated until the discarded solvent has reached the correct humidity level (Karl-Fischer method).

The resulting substance is then centrifuged and vacuum dried at a suitable temperature for 5–8 hours. The yield of this process is about 500–600 g of dry powder.

300 g of the dry powder is then submitted to an enzymatic digestion process with 0.2 g of suitable proteolytic agent (papain, pepsin, trypsin or pronase) through a buffered aqueous medium with a phosphate buffer using a quantity of cysteine hydrochloride to provide a ratio of 20:0.01 to 20:1 (w/w) between dry powder and cysteine hydrochloride. This mixture is then agitated for 24 hours at 60 rpm at a constant temperature of 60°–65° C. The whole mass is cooled to 25° C. adding 60 g of CELITE® and agitation is maintained for an additional hour.

The resulting mixture is filtered until a clear liquid is obtained.

The aqueous solution, diluted to 2 mg/ml with distilled water, is introduced into a column filled with a macromolecular ion-exchange resin DOWEX® M-15 obtained in the tetrabutylammonium (TBA+) form by means of treatment with tetrabutylammonium hydroxide.

The solution eluted from the column is evaporated and the dried residue is dissolved in a suitable volume of N-Methylpyrrolidone (or dimethylsulfoxide) to achieve a concentration of 2 mg/ml.

The obtained solution is filtered, cooled at 4° C. and an equal volume of water is added. Three subsequent washing processes are performed using methylene chloride and the lower phase is discarded each time. The upper phase is then treated with sodium bromide (NaBr is used at a molar ratio 3:1 with hyaluronic acid) at 4° C., the aqueous solution is precipitated by addition of 3 volumes of ethanol and the precipitate is washed several times with ethanol. The precipitate is solubilized in water and the resulting solution is submitted to dialysis. The solution is rendered 0.1M in NaCl by adding sodium chloride g.s. and the temperature is brought to 50° C. 45 g of cetylpyridinium chloride is added while the product is being agitated at 60 rpm. This mixture is agitated for 60 minutes, after which 50 g of CELITE® is added. Under agitation the temperature of the product is reduced to 25° C. and the precipitate formed is collected by means of centrifugation. The precipitate thus obtained is suspended in a 0.01M solution of sodium chloride (5 liters) containing 0.05% cetylpyridinium chloride. It is agitated for a further 60 minutes at 50° C. The temperature is lowered to 25° C. and the precipitate centrifuged.

The washing process is then repeated three times and the precipitate finally gathered into containers holding 3 liters of a 0.05M solution of sodium chloride containing 0.05% of cetylpyridinium chloride. This is agitated at 60 rpm for 60 minutes and maintained at a constant temperature of 25° C. for 2 hours. The supernatant is eliminated by means of centrifugation.

The procedure is repeated several times with a 0.1M sodium chloride solution containing 0.05% of cetylpyridinium chloride. The mixture is centrifuged and the supernatant discarded. The precipitate is dispersed in a 0.30M sodium chloride solution containing 0.05% of cetylpyridinium chloride (3:1).

The mixture is stirred and both the precipitate and the clear liquid are gathered. Extraction is repeated on the precipitate an additional 3 times, each time using 0.5 liters of the same aqueous solution.

The residue precipitate is eliminated and the clear liquids collected in a single container. The temperature of the liquid is increased to 50° C. while agitating. The liquid is then brought to 0.23M with sodium chloride. 1 g of cetylpyridinium chloride is added and agitation maintained for 12 hours. The mixture is cooled to 25° C. then filtered, first through CELITE® packs and then through a filter (1 μ).

The obtained solution then undergoes molecular ultrafiltration through membranes with a molecular exclusion limit of 30,000, ultrafiltering 3 original volumes with the addition of a 0.33M sodium chloride solution. The addition of the sodium chloride solution is suspended and the volume of the liquid reduced to a quarter of its original volume.

The solution thus concentrated is precipitated under agitation (60 rpm) at a temperature of 25° C. with three volumes of ethanol (95%). The precipitate is collected by centrifugation and the supernatant discarded. The precipitate is dissolved in 1 liter of 0.1M sodium chloride solution and the precipitation procedure is repeated with three volumes of 95% ethanol.

The precipitate is gathered and washed, first with 75% ethanol (three times), then with absolute ethanol (three times) and thirdly with absolute acetone (three times).

The product thus obtained (HA-1 fraction) has an average molecular weight ranging between 750,000 D and 1,230,000 D (preferably between 925,000 and 1,230,000).

The hyaluronic acid yield is equal to 0.6% of the original fresh tissue.

The final product, obtained by the previously described process, has the following characteristics:
molecular weight of 1,000,000 D.
limiting viscosity number ranging between 14.5 and 21 dl/g, when determined at 25° C. in 0.15M NaCl at pH 7.0 using an Ubbelhode suspended level viscosimeter. This corresponds to an average molecular weight ranging between 750,000 D and 1,230,000 D (preferably between 925,000 and 1,230,000).
a protein content not exceeding 0.2% expressed as Albumin, when determined by the Lowry test (Lowry J. et al.; Protein Measurement with the folin phenol reagent. J. Biol., Chem. 193, 265–275, 1951).
U.V. absorbance at 257 nm and at 280 nm not exceeding 1.0 A.U., when measured on a 1% w/V aqueous solution.
dynamic viscosity of a 1% solution w/v in 0.15M NaCl at pH=7.0, not exceeding the following limits at the defined shear rates, using a rotational viscosimeter such as those described in the U.S. Pharmacopea XXII ed. (911) page 1619, at a temperature of 20° C.

| Shear rate | Dynamic viscosity (mPa · s at 20° C.) |
| --- | --- |
| $1\ s^{-1}$ | not more than 20000 mPa · s |
| $10\ s^{-1}$ | not more than 2000 mPa · s |
| $100\ s^{-1}$ | not more than 1000 mPa · s |
| $350\ s^{-1}$ | not more than 500 mPa · s | a sulfated mucopolysaccharide content not exceeding 0.07% as sulfur, when determined on an inductively coupled plasma instrument (I.C.P.), using a suitable reference substance;
an iron content not exceeding 10 p.p.m., when determined by atomic absorption or I.C.P. technique.

A comparative study was carried out between HA-1 fraction and other hyaluronic acid sodium salt solutions obtained commercially, as regards their iron content.

The results obtained (Table 7) clearly indicate different iron contents: HA-1 fraction has an iron content which is much lower than that of the other products.

TABLE 7

| Iron content (ppm) of HA-1 versus other products | | | |
|---|---|---|---|
| | HA-1 | Sample A | Sample B | Sample C |
| Iron (ppm) | <10 | 130 | 120 | 40 | in which:
Sample A corresponds to SODICHIM (lot 154)
Sample B corresponds to BIOCHEMO (lot 542)
Sample C corresponds to BIOTECHNOLOGY GENERAL (lot B-25)
the iron ion content was determined on about 0.5 g of substance which had been calcined in a platinum crucible and the residue redissolved in $HNO_3$ 0.1M.
stability of isotonic buffered solutions with a physiological pH of the fraction HA-1, naturally aged and heat-sterilized, determined by assessment of the limiting viscosity number and expressed with the corresponding decrease in mean molecular weight, not exceeding the following limits:
97% of the initial value (storage at 25° C. for 6 months)
75% of the initial value (sterilization at 118° C. for 32 min.)
80% of the initial value (sterilization at 121° C. for 16 min.)
90% of the initial value (sterilization at 124° C. for 8 min.)

A comparative study was carried out between isotonic buffered solution with physiological pH of HA-1 and analogous solutions of hyaluronic acid, obtained commercially, to determine stability in conditions of:
natural aging (storage for 6 months at room temperature)
heat sterilization in various conditions Materials for pharmaceutical use and equipment which has already proved reliable for the described purposes were used.

These were in particular:
colorless glass vials with the following characteristics:
glass: type-1 borosilicate glass (according to Ph. Eur. II ed.)
minimum body thickness: 0.90 mm
maximum body thickness: 1.00 mm
Stoppers made of halobutylic rubber with the following characteristics:
  type of elastomer: chlorobutyl
  inert load: kaolin
  pigments: titanium dioxide and carbon black
  vulcanizing agent: zinc oxide
  release characteristics: according to Ph. Eur. II ed. VI.2.3.1
aluminum flip-off closures
water for injection (according to Ph. Eur. II ed.)
The reagents used were analytical grade.
A Fedegari autoclave, model FOF5 Superspectra, was used for sterilization.

The limiting viscosity number was determined with a suspended level, Ubbelhode-type viscosimeter at 25° C. in 0.15M NaCl at pH 7.0.

The corresponding mean molecular weight was calculated by the Mark-Houwink equation (H. Mark: Z. Elektrochemie 40, 499, 1934; R. Houwink: J. Prakt. Chem. 157, 15, 1940).

The mean molecular weight values were expressed as percentages of the starting value to better assess depolymerization trends. The results obtained (Tables 8 and 9) show that HA-1 has greater stability (at least twice as great) than the reference samples (see Table 7) which have a significantly higher iron content than HA-1.

TABLE 8 stability of the solution: effect of natural aging

| | Limiting viscosity number (dl/g) | | | variation in M.W. (%) | | |
|---|---|---|---|---|---|---|
| Sample | Initial | 3 months | 6 months | Initial | 3 months | 6 months |
| HA-1 | 20.9 | 20.8 | 20.5 | 100 | 99.4 | 97.5 |
| A | 10.4 | 10.1 | 9.6 | 100 | 96.2 | 89.9 |
| B | 9.7 | 9.2 | 8.8 | 100 | 93.2 | 87.8 |
| C | 15.5 | 15.1 | 14.8 | 100 | 96.6 | 94.0 |

TABLE 9

Stability of the solution: effect of sterilization

| | Limiting viscosity No. (dl/g) | | | | Variation in M.W. (%) | | | |
|---|---|---|---|---|---|---|---|---|
| Sample | Init. | I c. | II c. | III c. | Init. | I c. | II c. | III c. |
| HA-1 | 20.9 | 17.2 | 18.3 | 19.9 | 100 | 77.1 | 83.8 | 93.7 |
| A | 10.4 | 6.2 | 6.6 | 7.2 | 100 | 50.2 | 54.5 | 61.2 |
| B | 9.7 | 6.3 | 6.7 | 7.3 | 100 | 56.2 | 61.1 | 68.5 |
| C | 15.5 | 10.9 | 11.5 | 12.6 | 100 | 62.5 | 67.2 | 75.9 |

IC: sterilized at 118° C. for 32 minutes
IIC: sterilized at 121° C. for 16 minutes
IIIC: sterilized at 124° C. for 8 minutes.

in which:
Samples A, B, and C are the same as those used to determine the iron content
Solutions of approximately 10 mg/ml of each product in a 0.9% w/v solution of NaCl in phosphate buffer 0.002M pH 7.5 underwent:
a) natural aging, by being stored for 6 months at room temperature (25° C.), in the dark, with checks every three months (see Table 8)
b) sterilization in an autoclave in the following conditions:
  T=118° C. for 32 mins (indicated as Ic)
  T=121° C. for 16 mins (indicated as IIc)
  T=124° C. for 8 mins (indicated as IIIc) with checks at the start and finish of each condition.

Example 2—Procedure to Obtain HA-1 Fraction and its Relative Characterization

Hen crests, either fresh or frozen (3000 g), are minced in a meat mincer and then carefully homogenized in a mechanical homogenizer. The resulting paste is treated in a glass container with 4 volumes of 95% ethanol containing 0.1% w/v of a specific iron chelating agent.

1,10-Phenanthroline (C.A.R.N. 66–71–7) or its dimethyl derivatives are examples of useful chelating agents.

Glass containers and specific iron chelating agents are used to avoid the depolymerization process of hyaluronic acid sodium salt, which could otherwise be caused by iron ions from steel containers or blood residues.

The hen crests are treated until complete extraction of the iron ions (Instrumental control: Absorbance of complex iron-chelating agent in acetone or ethanol phase in 1-cm cells at wavelength of maximum absorption (510 nm, in the case of 1,10-(Phenanthroline, not more than 0.005 A.U.).

A further washing process is performed using the same volumes of anhydrous acetone (or ethanol) in order to remove any residue chelating agent. These treatments are carried out until the following test "A" results negative.

Test "A": 5 ml of acetone (or ethanol) phase are evaporated by means of moderate nitrogen flow. The residue is dissolved in 5 ml of water and the absorbance measured at wavelength of chelating agent maximum absorption.

The test is considered negative when absorbance is less than 0.1 A.U.

The final reaction product is stirred for 6 hours at a speed of 50 rpm and left to separate for 12 hours, after which the solvent is syphoned off and discarded.

This extraction process is repeated until the discarded solvent has reached the correct humidity level (Karl-Fischer method).

The resulting substance is then centrifuged and vacuum dried at a suitable temperature for at least 8 hours. The yield of this process is about 500–600 g of dry powder.

300 g of the dry powder is then submitted to an enzymatic digestion process with 0.2 g of suitable proteolytic agent (papain, pepsin, trypsin or pronase) through a buffered aqueous medium with a phosphate buffer using a quantity of cysteine hydrochloride to provide a ratio of 20:0.01 to 20:1 (w/w) between dry powder and cysteine hydrochloride. This mixture is then agitated for 24 hours at 60 rpm at a constant temperature of 60°–65° C. At the end of the reaction 60 g of CELITE® are added and the whole is agitated for an additional hour. The resulting mixture is filtered until a clear liquid is obtained.

45 g of cetylpyridinium chloride are added under agitation at 60 rpm. The mixture is agitated for 60 minutes, after which 50 g of CELITE® are added.

The precipitate thus formed is gathered by centrifugation and suspended in a solution of 0.01M of NaCl (5 liters) containing 0.05% cetylpyridinium.

It is agitated for 60 minutes at 50° C. and then brought to a temperature of 25° C. and the precipitate is centrifuged.

The washing procedure is repeated three times. The precipitate is gathered in containers holding 3 liters of 0.05M solution of sodium chloride containing 0.5% of cetylpyridinium chloride.

It is stirred at 60 rpm for 60 minutes and then kept at a constant temperature of 25° C. for two hours. The clear upper phase is eliminated by centrifugation.

The procedure is repeated twice with solutions of 0.1M sodium chloride containing 0.05% cetylpyridinium chloride. The mixture is centrifuged and the upper phase is discarded. The precipitate is dispersed in a solution of 0.30M sodium chloride containing 0.05% of cetylpyridinium chloride (3 liters).

The mixture is stirred and both the precipitate and the clear liquid are gathered. The precipitate is extracted a second time using 1.5 liters of the same aqueous solution.

The clear liquids are gathered in a single container and exposed to molecular ultrafiltration through membranes with a molecular exclusion cut-off of 30,000 Daltons, concentrating to a third of their initial volume.

The concentrated solution is treated with DOWEX® M-15 ion exchange macromolecular resin obtained in the form of tetrabutylammonium (TBA$^+$) and agitated overnight.

A suitable volume or N-methylpyrrolidone is added to the suspension till a ratio of NMP-H$_2$O 70/30 v/v is reached. The mixture is then filtered and the resin is eliminated.

A suitable quantity of NaCl is then added to the solution and brought to pH>7.5 with 1M NaOH and this is then washed twice with methylene chloride (CH$_2$Cl$_2$), discarding the lower phase each time. The upper phase is precipitated while agitating at 60 rpm at a temperature of 25° C. with three volumes of ethanol (95%).

The precipitate is gathered by centrifugation and the upper phase is discarded.

The precipitate is gathered and washed, first with 75% ethanol, then with absolute ethanol and lastly with acetone.

The washed product is then vacuum-dried for at least 20 hours at a temperature of 25° C. The dried product is solubilized in water by inverse osmosis so as to obtain a solution of >1 mg/ml. A suitable quantity of sodium chloride is added to obtain a molarity of between 0.1 and 0.4 and this is then made alkaline with 1M NaOH. The solution is then filtered through sterilizing filters.

The solution is precipitated while being stirred (60 rpm) at a temperature of 25° C. with three volumes of ethanol (95%).

The precipitate is gathered by centrifugation and the upper phase is discarded.

The precipitate is gathered and washed, first with 75% ethanol, then with absolute ethanol and finally with acetone.

The washed product is vacuum-dried for at least 50 hours at a temperature of 25° C.

The thus produced product has a molecular weight of 1,180,000.

EXAMPLES OF PHARMACEUTICAL PREPARATIONS

The following examples are presented here to describe, for illustrative purposes only, the possible pharmaceutical preparations for the therapeutic application of the fraction HA-1:

| Formulation 1: 2-ml ampules each ampule contains: | | |
|---|---|---|
| hyaluronic acid sodium salt (HA-1) | mg | 24.0 |
| monobasic sodium phosphate 2H$_2$O | mg | 0.1 |
| dibasic sodium phosphate 12H$_2$O | mg | 1.2 |
| sodium chloride | mg | 17.0 |
| water for injection to a volume of | ml | 2.0 |
| Formulation 2: sterile, ready-filled, 1.1-ml syringes each syringe contains: | | |
| hyaluronic acid sodium salt (HA-1) | mg | 20.0 |
| sodium chloride | mg | 9.350 |
| monobasic sodium phosphate 2H$_2$O | mg | 0.055 |
| dibasic sodium phosphate 12H$_2$O | mg | 0.660 |
| water for injection to a volume of | ml | 1.1 |
| Formulation 3: 0.2-ml, single-dose containers each container contains: | | |
| hyaluronic acid sodium salt (HA-1) | mg | 400.0 |
| sodium chloride | mg | 440.0 |
| monobasic sodium phosphate 2H$_2$O | mg | 5.0 |
| dibasic sodium phosphate 12H$_2$O | mg | 60.0 |
| water for injection to a volume of | ml | 100.0 |
| Formulation 4: 0.2-ml, single-dose containers each container contains: | | |
| hyaluronic acid sodium salt (HA-1) | mg | 200.0 |
| sodium chloride | mg | 670.0 |
| potassium chloride | mg | 250.0 |
| monobasic sodium phosphate 2H$_2$O | mg | 5.0 |
| dibasic sodium phosphate 12H$_2$O | mg | 60.0 |
| water for injection to a volume of | ml | 100.0 |

-continued

Formulation 5: 5-ml flacons
each flacon contains:

| | | |
|---|---|---|
| hyaluronic acid sodium salt (HA-1) | mg | 200.0 |
| sodium chloride | mg | 670.0 |
| potassium chloride | mg | 250.0 |
| monobasic sodium phosphate 2H$_2$O | mg | 5.0 |
| dibasic sodium phosphate 12H$_2$O | mg | 60.0 |
| sodium ethyl-Thimerosal (Chem. Abs. Reg. No. 54-64-8) | mg | 5.0 |
| water for injection to a volume of | ml | 100.0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A hyaluronic acid fraction, or a salt thereof, having a mean molecular weight in the range of 750,000 Daltons to 1,230,000 Daltons and having the following characteristics:
   a) limiting viscosity number ranging between 14.5 and 21 dl/g, when determined at 25° C. in 0.15M NaCl at pH 7.0 using an Ubbelhode suspended level viscosimeter;
   b) protein content not exceeding 0.2% expressed as albumin;
   c) a U.V. absorbance at 257 nm and at 280 nm not exceeding 1.0 A.U., when measured on a 1% weight per volume aqueous solution;
   d) a dynamic viscosity of a 1% weight per volume solution in 0.15 NaCl at pH=7.0, not exceeding the following limits at the defined shear rates, using a rotational viscosimeter at a temperature of 20° C.:

| Shear rate | Dynamic viscosity (mPa · s at 20° C.) |
|---|---|
| 1 s$^{-1}$ | not more than 20000 mPa · s |
| 10 s$^{-1}$ | not more than 2000 mPa · s |
| 100 s$^{-1}$ | not more than 1000 mPa · s |
| 350 s$^{-1}$ | not more than 500 mPa · s | e) a sulfated mucopolysaccharide content not exceeding 0.07% as sulfur;
   f) an iron content not exceeding 10 p.p.m.; and
   g) stability of isotonic buffered solutions with a physiological pH of the fraction, naturally aged and heat-sterilized, determined by assessment of the limiting viscosity number and expressed with the corresponding decrease in mean molecular weight, not exceeding the following limits:
   the actual value after storage at 25° C. for 6 months must not be lower than 97% of the initial value
   the actual value after sterilization at 118° C. for 32 minutes must not be lower than 75% of the initial value
   the actual value after sterilization at 121° C. for 16 minutes must not be lower than 80% of the initial value
   the actual value after sterilization at 124° C. for 8 minutes must not be lower than 90% of the initial value.

2. A hyaluronic acid fraction according to claim 1, wherein said mean molecular weight is between 925,000 and 1,230,000 Daltons.

3. A process for the purification of hyaluronic acid or a salt thereof, which comprises:
   a) converting hyaluronic acid or a salt thereof into a corresponding quaternary ammonium salt;
   b) dissolving said corresponding quaternary ammonium salt in an organic solvent capable of dissolving such ammonium salts; and
   c) filtering the solution and treating with a sodium halogenide to recover the hyaluronic acid in the form of a sodium salt.

4. The process according to claim 3, wherein said quaternary ammonium salt is formed by absorption of an aqueous solution of said salt of hyaluronic acid onto an acid ion exchanger salified with a quaternary ammonium base.

5. The process according to claim 4, wherein said ion exchanger is a strong cationic exchanger with sulfonic groups in a quaternary ammonium form.

6. The process according to claims 3, 4 or 5, wherein said organic solvent used to dissolve the quaternary ammonium salt of hyaluronic acid is an aprotic solvent.

7. The process according to claim 6, wherein the aprotic solvent is a lower dialkylsulfoxide or dialkylcarboxylamide.

8. The process according to claim 7, wherein said aprotic solvent is dimethylsulfoxide or N-methyl-pyrrolidone.

9. The process according to claim 3, wherein said salt of hyaluronic acid to be converted is a sodium salt and wherein said organic solvent is an aprotic solvent.

10. The process according to claim 9, wherein conversion of the ammonium salt of hyaluronic acid into the corresponding sodium salt of hyaluronic acid is conducted by the addition of sodium bromide to the solution of the ammonium salt of hyaluronic acid in said aprotic solvent.

11. A process for the preparation of a fraction of hyaluronic acid which comprises
   a) extracting hyaluronic acid from an animal organ with a first organic solvent in the presence of an iron-chelating agent to obtain a hyaluronic acid-containing extract which is substantially free of iron ions;
   b) treating said hyaluronic acid-containing extract with a proteolytic agent;
   c) contacting the thus treated hyaluronic acid-containing extract with an acid ion exchanger in the form of a quaternary ammonium salt;
   d) dissolving the extract from the ion exchanger in a second organic solvent which is capable of dissolving a quaternary ammonium salt of hyaluronic acid;
   e) treating the mixture of step (d) with a sodium halogenide to convert the quaternary ammonium salt of hyaluronic acid to the corresponding sodium salt; and
   f) isolating the desired sodium salt of hyaluronic acid.

12. The process according to claim 10, wherein an aqueous solution of said sodium salt of hyaluronic acid is subjected to molecular filtration to obtain a desired molecular weight fraction of said sodium salt of hyaluronic acid.

13. The process according to claim 12, wherein said acid ion exchanger is a sulfonic resin in the form of a quaternary ammonium salt.

14. The process according to claim 13, wherein said quaternary ammonium salt is a tetraalkylammonium salt having an alkyl group with a maximum of 6 carbon atoms.

15. The process according to claim 14, wherein said tetraalkylammonium salt is a tetrabutylammonium salt.

16. The process according to claim 11, wherein said first organic solvent is ethanol or acetone; and said iron chelating agent is 1,10-phenanthroline.

17. The process according to claim 11, wherein said sodium salt is treated with a sterilization agent.

18. The process according to claim 17, wherein said sterilization agent is cetylpyridinium chloride.

19. The process according to claim 12, wherein said sodium salt of hyaluronic acid is subjected to molecular filtration with a membrane having a molecular exclusion limit of 30,000 Daltons.

20. A process for the preparation of a fraction of sodium hyaluronate which comprises:

a) extracting organic material from hen crests with an extraction solvent comprised of acetone or ethanol and phenanthroline or phenanthroline to produce an extract which is substantially free of iron ions;

b) treating said extract with a proteolytic agent selected from the group consisting of papain, pepsin, trypsin, pronase and cysteine hydrochloride;

c) contacting the thus treated extract with a column filled with a sulfonic acid resin in the form of tetrabutylammonium salt;

d) eluting the column to obtain a solution containing the tetrabutylammonium salt of hyaluronic acid;

e) drying the solution to obtain a residue comprised of the tetrabutylammonium salt of hyaluronic acid;

f) dissolving said residue in an aprotic solvent;

g) filtering the solution of step (f);

h) washing the solution of step (g) with methylene chloride;

i) treating the solution of step (h) with a sodium halogenide to produce sodium hyaluronate;

j) precipitating said sodium hyaluronate;

k) dissolving the precipitate in water and subjecting the solution to dialysis;

l) precipitating sodium hyaluronate from the dialyzed solution; and m) subjecting said precipitate to molecular filtration with a membrane having a molecular exclusion limit of 30,000 Daltons, to produce a solution containing the sodium salt of hyaluronic acid having an average molecular weight of between 750,000 and 1,230,000 Daltons.

21. The sodium hyaluronate fraction prepared by the process of claim 20.

22. A pharmaceutical preparation containing as the active ingredient the hyaluronic acid fraction according to claim 1 together with pharmaceutical excipients.

23. In a method of performing ocular surgery, the improvement which comprises the use of the hyaluronic acid fraction of claim 11.

24. In a method of performing procedures in ophthalmology, the improvement which comprises the use of the hyaluronic acid fraction of claim 11.

25. In a method of performing cataract operations or ocular lens implants, the improvement which comprises the use of the hyaluronic acid fraction of claim 1.

* * * * *